(12) United States Patent
Kim et al.

(10) Patent No.: US 9,259,493 B2
(45) Date of Patent: Feb. 16, 2016

(54) LIVER TUMOR-TARGETING ULTRASOUND CONTRAST AGENT AND METHOD FOR PREPARING THE SAME

(71) Applicant: KOREA INSTITUTE OF SCIENCE AND TECHNOLOGY, Seoul (KR)

(72) Inventors: Kwang Meyung Kim, Seoul (KR); Ick Chan Kwon, Seoul (KR); Inchan Youn, Seoul (KR); Hyun Su Min, Daejeon (KR); Hong Yeol Yoon, Hwaseong (KR); Jae Hyung Park, Suwon (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 96 days.

(21) Appl. No.: 14/074,865

(22) Filed: Nov. 8, 2013

(65) Prior Publication Data

US 2014/0140934 A1    May 22, 2014

(30) Foreign Application Priority Data

Nov. 21, 2012  (KR) ........................ 10-2012-0132401

(51) Int. Cl.
*A61K 49/22* (2006.01)
*A61K 49/00* (2006.01)

(52) U.S. Cl.
CPC ........... *A61K 49/223* (2013.01); *A61K 49/0032* (2013.01); *A61K 49/0069* (2013.01)

(58) Field of Classification Search
None
See application file for complete search history.

(56) References Cited

U.S. PATENT DOCUMENTS

| 5,362,478 A * | 11/1994 | Desai et al. | 424/9.322 |
| 6,193,951 B1 | 2/2001 | Ottoboni et al. | |
| 2011/0104069 A1 * | 5/2011 | Xu et al. | 424/9.6 |

OTHER PUBLICATIONS

Ki Su Kim et al., "Bioimaging for Targeted Delivery of Hyaluronic Acid Derivatives to the Livers in Cirrhotic Mice Using Quantum Dots", ACS NANO, vol. 4, No. 6, 2010, pp. 3005-3014.
Ki Young Choi et al., "Self-Assembled Hyaluronic Acid Nanoparticles as a Potential Drug Carrier for Cancer Therapy: Synthesis, Characterization, and in vivo Biodistribution", Journal of Materials Chemistry, vol. 19, No. 24, Jun. 28, 2009, pp. 4102-4107 (with a cover page).

* cited by examiner

*Primary Examiner* — Michael G Hartley
*Assistant Examiner* — Jennifer Lamberski
(74) *Attorney, Agent, or Firm* — Goldilocks Zone IP Law (57) ABSTRACT

Disclosed is a liver tumor-targeting ultrasound contrast agent. The ultrasound contrast agent includes a gas-generating core and a hyaluronic acid shell. The ultrasound contrast agent can be specifically delivered to liver cells. This specific delivery enables easy differentiation between normal liver cells and liver tumor cells by ultrasound imaging. In addition, the ultrasound contrast agent is highly stable in aqueous condition and causes no cytotoxicity. Also disclosed is a method for preparing the ultrasound contrast agent.

8 Claims, 12 Drawing Sheets

LIVER TUMOR-TARGETING ULTRASOUND CONTRAST AGENT AND METHOD FOR PREPARING THE SAME

CROSS-REFERENCE TO RELATED APPLICATIONS

This application claims priority under 35 U.S.C. §119 to Korean Patent Application No. 10-2012-0132401 filed on Nov. 21, 2012, in the Korean Intellectual Property Office, the disclosure of which is incorporated herein by reference in its entirety.

BACKGROUND OF THE INVENTION

1. Field of the Invention

The present invention relates to an ultrasound contrast agent that uses particles specifically targeting a liver site, and a method for preparing the ultrasound contrast agent.

2. Description of the Related Art

Ultrasound (US) imaging is the most frequently used imaging modality during diagnosis in clinical fields. It has no time-delay to obtain images, and is relatively cheap, non-invasive, safe, and easy for handling. To obtain more advanced information by ultrasound imaging, various ultrasound contrast agents have been developed, and applied to diagnosis. In general, most of them are microbubbles which are composed of gas cores such as $N_2$ or perfluorocarbons and outer shells such as lipids or polymers. Ultrasound contrast agents can oscillate in response to acoustic pulse and provide bright signals in ultrasound images. Consequently, the localization and movement of these bright signals have been used for precise ultrasound imaging such as blood flow analysis.

In this century, the target-specific delivery of ultrasound contrast agents has garnered large amount of attention from many researchers. It is based on biological interactions and can provide molecular-level information as well as anatomical one. These targeted ultrasound contrast agents have been developed by conjugating antibodies, aptamers, or peptides on their shell. They can bind to special receptors on the surface of target cells and increase the accumulation of ultrasound contrast agent in target site.

Hyaluronic acid (HA) is one of the human body glycosaminoglycans and is non-toxic and biodegradable in body condition by enzymes like hyaluronidase. The chemical structure of hyaluronic acid is repeating disaccharides of N-acetyl-D-glucosamine and D-glucuronic acid bearing many carboxylic acids which can be used for further chemical modification. Especially, hyaluronic acid can bind to CD44 receptors which are overexpressed in liver. Consequently, hyaluronic acid can be used as attractive component of imaging agents to increase the target-specific delivery of ultrasound contrast agents for optical or MR imaging of liver.

SUMMARY OF THE INVENTION

Therefore, the present invention is directed to providing an ultrasound contrast agent that can target a liver site due to its ability to specifically bind to CD44 receptors overexpressed in liver cells, is highly stable in vivo, and causes no cytotoxicity despite its accumulation in liver cells, and a method for preparing the ultrasound contrast agent.

According to one aspect of the present invention, there is provided a liver tumor-targeting ultrasound contrast agent including a gas-generating core and a hyaluronic acid shell.

In one embodiment of the present invention, the gas-generating core may be a $C_1$-$C_6$ perfluorocarbon compound.

In a further embodiment of the present invention, the hyaluronic acid may be a hydrophobically modified hyaluronic acid.

In another embodiment of the present invention, the ultrasound contrast agent may include 100 parts by volume of the hyaluronic acid shell and 0.08 to 5 parts by volume of the gas-generating core.

In another embodiment of the present invention, the ultrasound contrast agent may have an average particle diameter of 400 nm to 4 µm.

In another embodiment of the present invention, the ultrasound contrast agent may further include a fluorescent marker attached to the hyaluronic acid shell.

According to another aspect of the present invention, there is provided a method for preparing a liver tumor-targeting ultrasound contrast agent, including:

hydrophobically modifying hyaluronic acid;

purifying and drying the modified hyaluronic acid, followed by dissolution in deionized water; and dropping a gas-generating compound into the hyaluronic acid solution.

In one embodiment of the present invention, the hyaluronic acid may be hydrophobically modified by reaction with 5β-cholanic acid.

In a further embodiment of the present invention, the gas-generating compound may be a $C_1$-$C_6$ perfluorocarbon compound.

In another embodiment of the present invention, the gas-generating compound may be used in an amount of 0.08 to 5 parts by volume, based on 100 parts by volume of the hyaluronic acid.

In another embodiment of the present invention, the method may further include subjecting the mixed solution to sonication after dropping of the gas-generating compound.

Liver cell-specific delivery of the liver tumor-targeting ultrasound contrast agent according to the present invention enables easy differentiation between normal liver cells and liver tumor cells by ultrasound imaging. In addition, the ultrasound contrast agent of the present invention is highly stable in aqueous condition and causes no cytotoxicity. The method of the present invention is suitable for the preparation of the ultrasound contrast agent.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

The present invention will now be described in more detail.

The present inventors have found the fact that HA-coated microbubbles (HAMBs) can be efficiently accumulated in liver by CD44 receptor binding, and they can be successfully used for in vivo liver diagnosis based on ultrasound imaging. The present invention has been accomplished based on this finding. Specifically, with the possibility of HA that can be used as shell materials of many nano- or microparticles, the present inventors developed HAMBs and evaluated the potential of HAMBs as ultrasound contrast agent. Their stability and ultrasound signal generation was evaluated in aqueous condition, as can be seen from the Examples section that follows. Because HAMBs are expected to be efficiently accumulated in liver by CD44 receptor binding, their in vivo biodistribution in mice was tested by optical imaging. Then, the potential of HAMBs as ultrasound contrast imaging agent in normal and liver tumor-bearing mice models was evaluated.

Figure 1:
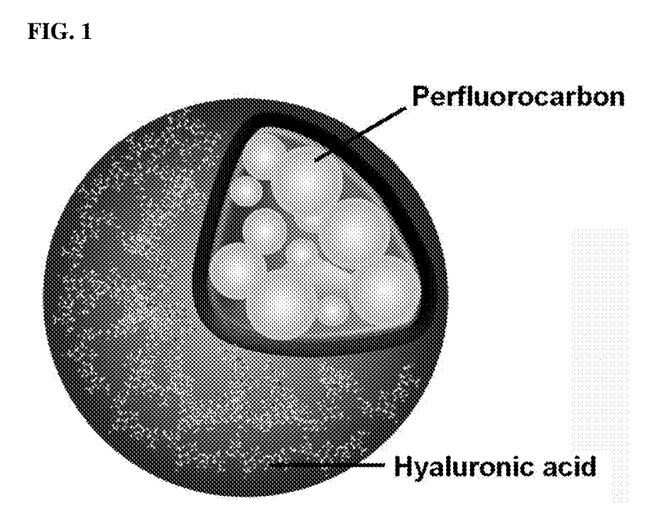
FIG. 1 is a schematic diagram showing a contrast agent of the present invention.
Figure 2A:
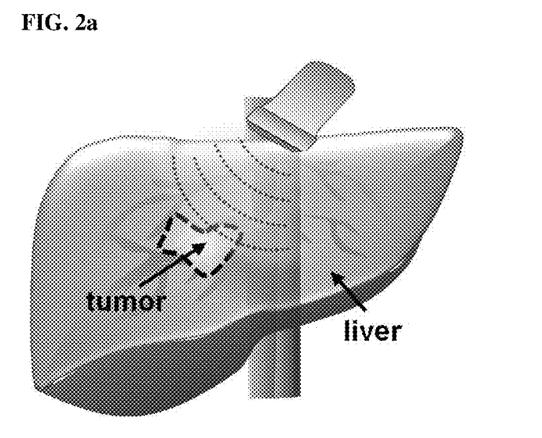
FIG. 2a is a schematic diagram showing the diagnosis of a tumor site using an ultrasound diagnostic system after administration of a contrast agent according to the present invention.
Figure 2B:
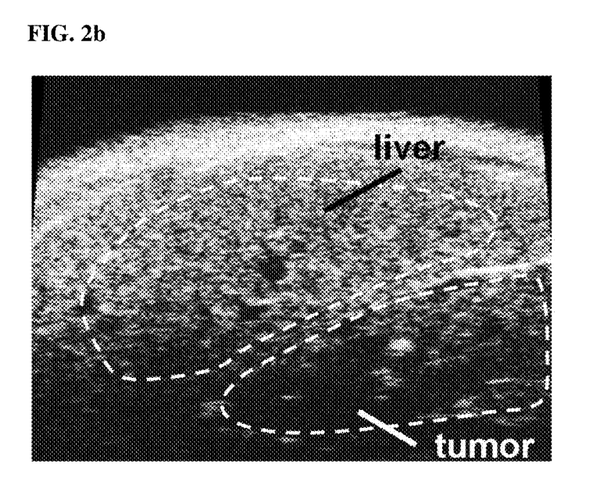
FIG. 2b is an actual ultrasound image of liver taken during diagnosis.

Thus, the present invention provides a liver tumor-targeting ultrasound contrast agent including a gas-generating core and a hyaluronic acid shell. FIG. 1 is a schematic diagram showing the contrast agent of the present invention. Referring to FIG. 1, the gas-generating core is a component that oscillates in response to acoustic pulse to generate bright signals in ultrasound images, and the hyaluronic acid shell is a component that binds to CD44 receptors overexpressed in liver, which ensures liver cell-specific targeting of the ultrasound contrast agent according to the present invention. FIG. 2a is a schematic diagram showing the diagnosis of a tumor site using an ultrasound diagnostic system after administration of the contrast agent according to the present invention, and FIG. 2b is an ultrasound image of liver taken using the contrast agent of the present invention.

The gas-generating core may be a $C_1$-$C_6$ perfluorocarbon compound. The gas-generating core may be any of those commonly used as gas-generating components of ultrasound contrast agents in the art. An example of the gas-generating core may be perfluoropentane.

Hyaluronic acid as a component of the ultrasound contrast agent according to the present invention is an amphiphilic substance. Hyaluronic acid may be modified, for example, by treatment with a hydrophobic acid. In this case, the modified hyaluronic acid can be self-assembled in aqueous condition to form nanoparticles.

Preferably, the ultrasound contrast agent of the present invention includes 100 parts by volume of the hyaluronic acid shell and 0.08 to 5 parts by volume of the gas-generating core. The presence of the gas-generating core in an excess amount outside this range may lead to excess gas generation, which impedes blood flow in blood vessel, and poor in vivo stability of the contrast agent particles. Meanwhile, the presence of the hyaluronic acid in an excess amount may undesirably deteriorate the efficacy of the ultrasound contrast agent and the solubility of the particles in aqueous solution.

The ultrasound contrast agent of the present invention is spherical in shape, has an average particle diameter of 400 nm to 4 μm in aqueous condition, and is maintained stable for a long time. In addition, a fluorescence marker such as Cy5.5 may be attached to the shell of the ultrasound contrast agent. In this case, the contrast agent can be traced in vivo by using a fluorescence analysis system.

The present invention also provides a method for preparing a liver tumor-targeting ultrasound contrast agent, including: hydrophobically modifying hyaluronic acid; purifying and drying the modified hyaluronic acid, followed by dissolution in deionized water; and dropping a gas-generating compound into the hyaluronic acid solution.

Figure 3:
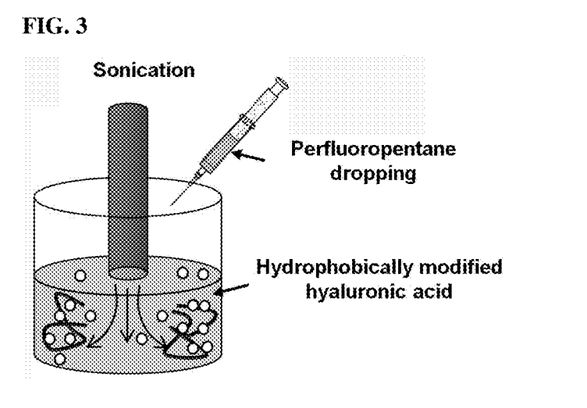
FIG. 3 is a schematic diagram showing a procedure in which a hydrophobically modified hyaluronic acid is dissolved, perfluoropentane as a gas-generating compound is dropped into the hyaluronic acid solution, and the resulting solution is stirred.

As described above, the hydrophobic modification is performed to form self-assembled nanoparticles in aqueous condition. For example, the hyaluronic acid may be hydrophobically modified by reaction with 53-cholanic acid. FIG. 3 is a schematic diagram showing a procedure in which the hydrophobically modified hyaluronic acid is dissolved, perfluoropentane as the gas-generating compound is dropped into the hyaluronic acid solution, and the resulting solution is stirred. As shown in FIG. 3, sonication is preferably performed for an appropriate time to facilitate the formation of microbubbles in the form of capsules.

The kind of the compound for forming a gas-generating core and the amount of hyaluronic acid relative to the gas-generating compound are the same as those described above.

The present invention will be explained in more detail with reference to the following examples. However, these examples are given to assist in understanding the invention and are not to be construed as limiting the scope of the invention.

Materials and Methods

Materials

Sodium hyaluronate (Mw 250 KDa) was purchased from Lifecore Biomedical (Chaska, Minn.), purified by washing with deionized water and lyophilized after dialysis against distilled water. 5β-cholanic acid, N-hydroxysuccinimade (NHS), 1-ethyl-3-(3-dimethylaminopropyl)-carbodiimide hydrochloride (EDC) were purchased from Sigma Chemical Co. (St. Louis, Mo.). Perfluoropentane 99% was obtained from Apollo Scientific Ltd. (Manchester, UK).

Preparation of Hydrophobically Modified Hyaluronic Acid

Hydrophobically modified hyaluronic acid was prepared using chemical conjugate of hyaluronic acid with 5β-cholanic acid. To prepare the chemical conjugate of hydrophobically modified hyaluronic acid, each hyaluronic acid and 5β-cholanic acid were dissolved in water and methanol. First, EDC and NHS were progressively added to 5β-cholanic acid solution to activate carboxylic acid groups. Then, the activated 5β-cholanic acid solution was slowly dropped into the hyaluronic acid solution. The mixture was maintained for 24 hours with stirring at room temperature. The reaction mixture was purified after reaction by dialysis of reactant against water/methanol (1:4) then lyophilized. The hydrophobic hyaluronic acid conjugate thus prepared has a repeating unit represented by Formula 1.

HAMBs Characterization

The size distribution of HAMBs was measured by dynamic light scattering (DLS, Spectra Physics, CA, USA). 10% of diluted HAMBs emulsion in deionized water was measured with the increase of time until 3 hours at 37° C. Size and bubble increase properties were also visualized by optical microscope (BX51; Olympus Co. Ltd., Japan) equipped with 40× focal lens. The HAMBs were kept in water bath at 37° C., the samples were taken off every 10 min and microscopic images were obtained until 3 hours.

Cytotoxicity of HAMBs 3-(4,5-Dimethylthiazol-2-yl)-2,5-diphenyltetrazolium bromide (MTT) assay was conducted to evaluate the cytotoxicity of HAMBs using Squamous cell carcinoma (SCC-7) cells in vitro. SCC-7 cells were cultured with the mixture of antibiotics (1%) and fetal bovine serum (10%) in RPMI solution. After seeding of SCC-7 cells on 96-well tissue culture plate at $1\times10^4$ cells/well, 200 μL of diluted HAMBs (1 μg-10 mg/mL) with cell culture medium were added into the cells. Then, the cells were incubated under $CO_2$ atmosphere at 37° C. for 24 hours. After dropping of MTT-containing medium (1)

Formulation

Hyaluronic acid-coated microbubbles were prepared using conventional emulsion method just adding of perfluorocarbon into HA solution. Hydrophobically modified HA was dissolved in deionized water at a concentration of 4 mg/mL and the solution was filtered using a 0.45 μm syringe filter (Whatman Int. Ltd., Springfield Mill, UK). The HA solution was moved to an ice container and located a probe type sonicator (Ultrasonic processor 750-Watt, Cole-Parmer®, IL, USA). And 1% volume of PFP was slowly added to the HA solution using a syringe and the mixture was sonicated by 25% of power for 2 minutes. Then, the PFP encapsulated microbubbles were formed into an emulsion.

to the cells, the cells were incubated for 2 hours to stain the MTT solution. The absorbance was measured using Micro plate reader (VERSAmax™, Molecular Devices Corp., Sunnyvale, Calif.) at 570 nm and the cell viability was calculated.

Cellular Uptake Behavior of HAMBs

Cy5.5-containing HAMBs were prepared using Cy5.5-labeled hyaluronic acid to evaluate the HAMBs in cellular level using optical microscope. Chang's liver (CL) cells were incubated with RPMI cell culture medium with 10% fetal bovine serum (FBS). For affinity study of HAMBs to normal liver cell, competitive inhibition experiment was conducted using HA polymer. HAMBs were treated into CL cell with or without serum free culture medium containing HA polymer (10 mg/ml) before incubation for 15 minutes. The cells were incubated for 90 minutes, washed twice with PBS and fixed with paraformaldehyde (4%) solution. Cellular uptake images of HAMBs were observed using a fluorescence microscope (IX81, Olympus, Japan) with Cy5.5 filter (Ex=673 nm, Em=692 nm).

Fluorescence Imaging In Vivo

All animal experiments with animals were conducted according to the relevant laws and institutional guidelines of Korea Institute of Science and Technology (KIST) and institutional committees. Cy5.5 dye-labeled Pluronic was used for preparing HAMBs to trace the particle moiety in vivo. 5.5 weeks old male C3H/HeN mice (n=4 per each group) were used for imaging and fluorescence images were obtained by eXploreOptix system (Advanced Research Tech. Inc., Montreal, Canada). Abdominal hair of mice was removed after anesthetizing using isoflurane gas. For the first group of mice, free HA solution (4 mg/mL) was administered and 5 minute after HAMBs were injected again into tail vein whereas for the second group of mice, HAMBs only were injected. The fluorescence images of liver were obtained according to the time up to 3 hours at 50 µW of laser power. All the mice were sacrificed at 3 hours after i.v. injection, liver was excised and fixed with formaldehyde (4%, w/v) solution. Residual fluorescence intensity of liver was analyzed using Kodak imaging station (Image Station 4000 mm; Kodak, New Haven, Conn.) attached with 12-bit CCD camera and Cy5.5 emission filter (600-700 nm; Omega Optical).

Ultrasound Contrast Enhancement In Vitro

In vitro study, ultrasound images were obtained at agar-gel phantom using Vevo770® (High-Resolution Micro-Imaging System, Visualsonics, Toronto, Canada) equipped with RMV 706 probe. All the samples were kept at 37° C. before use and in vitro test was conducted in hand-made agar-gel phantom to make the similar condition to body. In brief, a 500 µL Eppendorf tube was embedded in agar-gel (3%, w/v), cooled down at room temperature, and removed. For in vitro imaging, 300 µL of HAMBs were administered to agar-phantom and 40 MHz of ultrasound frequency was applied using Vevo770® system. Ultrasound images were obtained according to the concentration (0.08%-5%, w/v) of PFP and the time until 3 hours at 37° C.

Ultrasound Contrast Enhancement of Liver 5.5 weeks old male C3H/HeN mice (n=3, 25-30 g) were anesthetized using isofluorane gas and abdominal hair was removed with depilatory cream. Mice were located in animal pad (Vevo770® maintaining at 37° C.) and liver site was imaged using RMV706 probe. After obtaining of free injected liver images, 300 µL of HAMBs were injected into the tail vein and all the images was taken as video file. The ultrasound imaging of liver was performed according to time up to 3 hours and contrast enhancement was calculated with the subtracted ROI ratio between background to normal liver tissue.

Ultrasound imaging of liver cancer

Human colonic carcinoma cell line (HT29) was cultured in RPMI cell culture medium containing 10% FBS and penicillin G/streptomycin at 37° C. Liver cancer model of C3H/HeN (n=3, 25-30 g) mice was made using surgical injection of human colonic carcinoma (HT29) cell ($3\times10^5$) into the liver. Tumor size was checked at B-Mode of Vevo770® system which could detect morphology of liver. After tumor volumes grew up to 50 mm³, 300 µL of HAMBs were intravenously injected and 40 MHz of ultrasound was applied for vivo imaging. Then, ultrasound images of liver cancer were obtained at Contrast-Mode and time dependent contrast enhancement was evaluated up to 1 hour.

Results and discussion

Preparation and characterization of hyaluronic acid-coated microbubbles (HAMBs)

HAMBs were prepared using amphiphilic HA conjugates and perfluoropentane. Hydrophobic 5β-cholanic acids were conjugated to HA backbone via amide bonds. The resulting amphiphilic HA conjugates self-assembled in aqueous condition and formed nanoparticles. Then, perfluoropentane was loaded to these HA nanoparticles using 0/W emulsion method by sonication of perfluoropentane into HA solution.

Figure 4A:
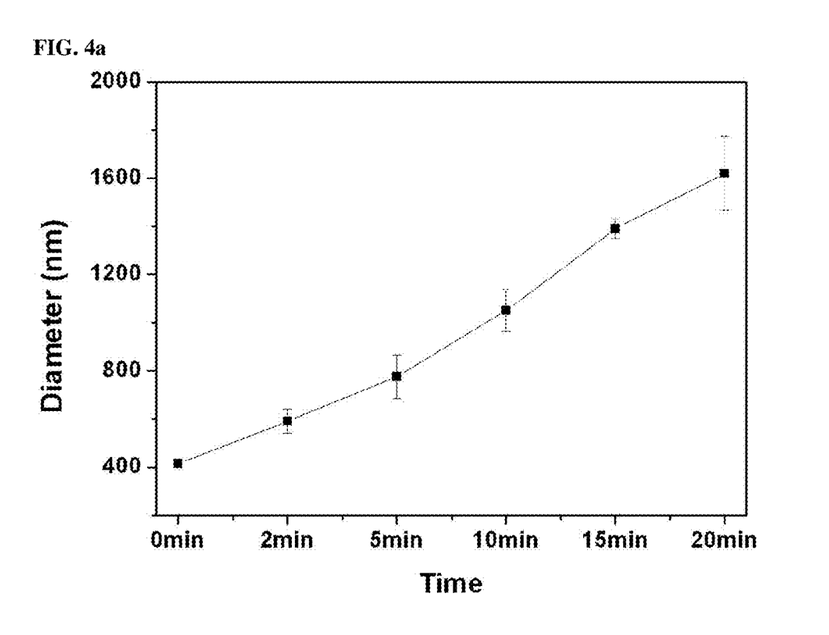
FIG. 4a shows size changes of hyaluronic acid-coated microbubbles (HAMBs) via time (0, 2, 5, 10, 15, and 20 minutes) for 20 minutes.
Figure 4B:
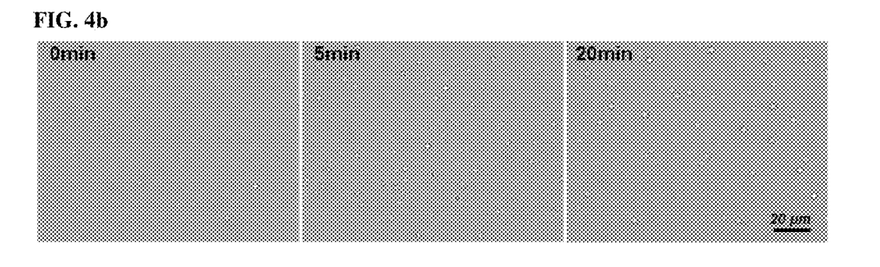
FIG. 4b shows microscopic images of the particle size after 0, 5, and 20 minutes.

FIG. 4a shows size changes of HAMBs via time (0, 2, 5, 10, 15, and 20 minutes) for 20 minutes, and FIG. 4b shows microscopic images of the particle size after 0, 5, and 20 minutes. After perfluoropentane loading, the size changes of particles from 415 nm to 1650 µm significantly showed the formation of HAMBs. Without nanoparticles, perfluoropentane could not be stabilized into micro-sized bubbles in aqueous condition. The size distribution of HAMBs from 1450 to 1800 nm did not remarkably changed at 37° C. after 6 hours, showing the stability of these HAMBs. The spherical shape and micrometer-size of HAMBs also could be observed in microscopic images.

Figure 5A:
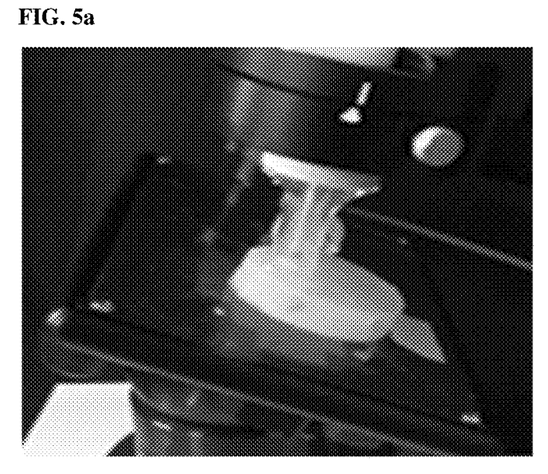
FIG. 5a is a photograph of hand-made agar-gel where in vitro ultrasound images were observed.
Figure 5B:
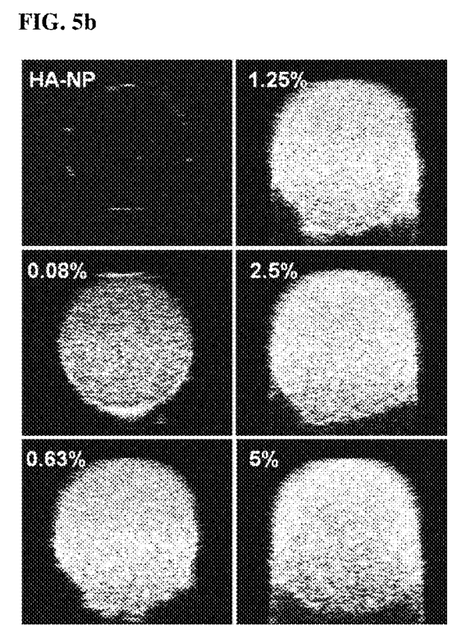
FIG. 5b shows in vitro ultrasound images observed at perfluoropentane concentrations of 0%, 0.08%, 0.63%, 1.25%, 2.5%, and 5%.
Figure 5C:
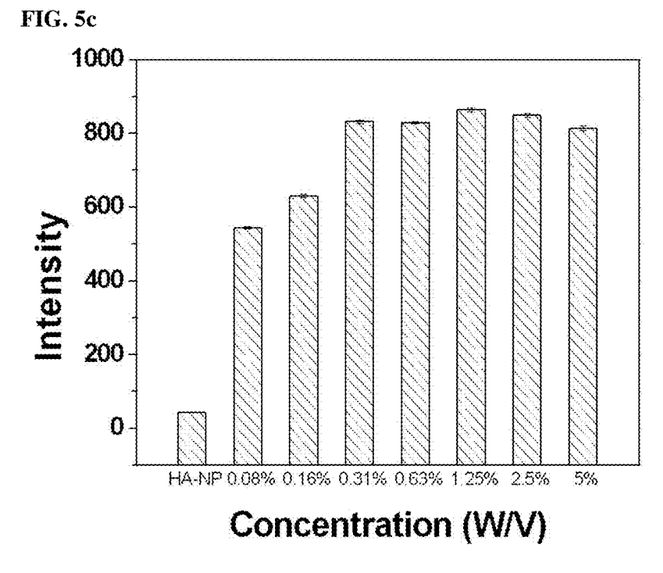
FIG. 5c is a graph showing the relative intensities of the in vitro ultrasound images via the respective concentrations.

In vitro ultrasound images of HAMBs were obtained using agar-gel phantom. FIG. 5a is a photograph of hand-made agar-gel where in vitro ultrasound images were observed, FIG. 5b shows in vitro ultrasound images observed at perfluoropentane concentrations of 0%, 0.08%, 0.63%, 1.25%, 2.5%, and 5%, and FIG. 5c is a graph showing the relative intensities of the in vitro ultrasound images via the respective concentrations.

Above the concentration of 0.25 mg/ml, HAMBs generated intense ultrasound signals, which was maximized at 1 mg/ml. The ultrasound signal intensity was about 865 AU and about 20-fold higher than sole hyaluronic acid nanoparticles and perfluoropentane. These ultrasound signals were maintained for about 2 hours due to their superior stability.

Figure 6A:
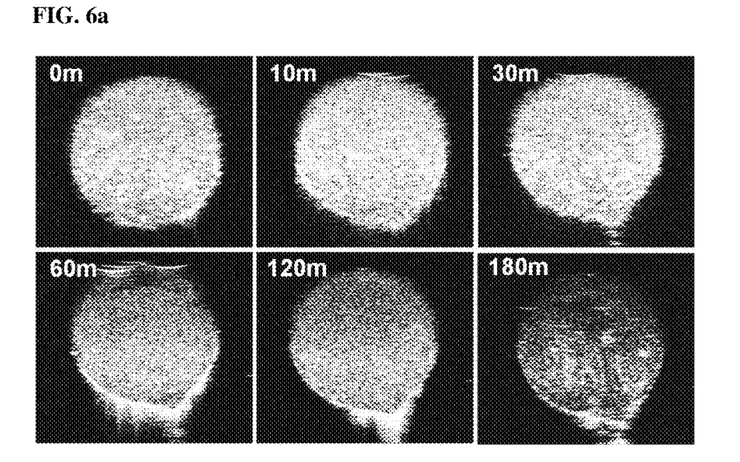
FIG. 6a shows time-dependent ultrasound images observed in vitro for 3 hours.
Figure 6B:
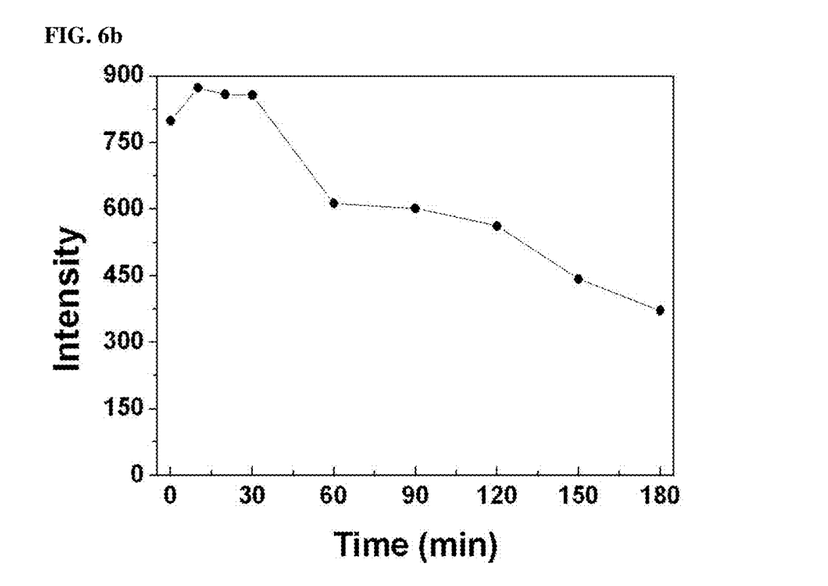
FIG. 6b is a graph showing the intensities of the ultrasound images with the time.

FIG. 6a shows time-dependent ultrasound images observed in vitro for 3 hours, and FIG. 6b is a graph showing the intensities of the ultrasound images with the time.

In Vitro Binding of HAMBs to Liver Cells and Cell Viability Test

The binding of HAMBs to liver cells based on the interaction with CD44 receptors was evaluated in cellular images. HAMBs were labeled with near-infrared (NIRF) dye, 10 mg/mL of hyaluronic acid polymer, and treated to Chang's liver (CL) cells. After 90 min incubation, intense red spots of HAMBs on the surface of cells showed fast and efficient binding of HAMBs to liver cells.

Figure 7A:
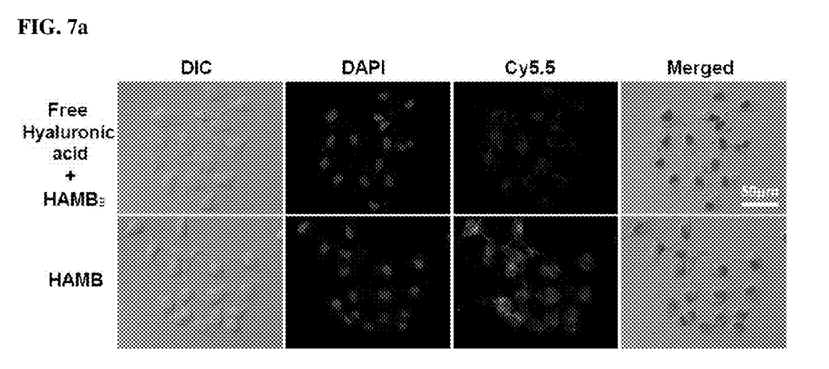
FIG. 7a shows differential interference contrast (DIC) microscopy images, fluorescence images observed after staining with DAPI, fluorescence images observed using Cy5.5-labeled HAMBs, and their merged images on a sample pretreated with free hyaluronic acid and a sample without pretreatment with free hyaluronic acid.
Figure 7B:
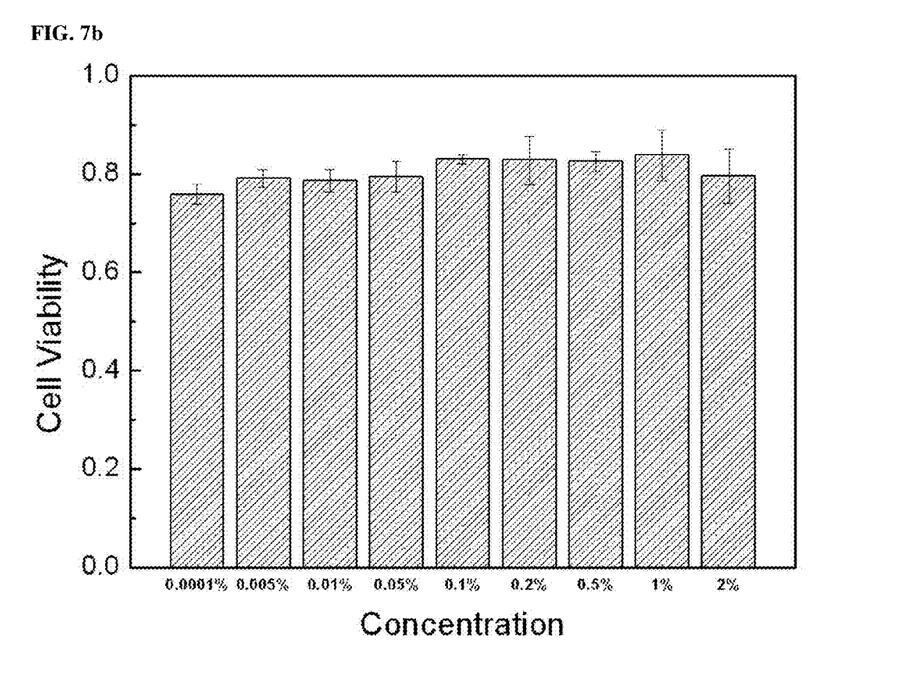
FIG. 7b shows cell viability at different concentrations of HAMBs.

FIG. 7a shows differential interference contrast (DIC) microscopy images, fluorescence images observed after staining with DAPI, fluorescence images observed using Cy5.5-labeled HAMBs, and their merged images on a sample pretreated with free hyaluronic acid and a sample without pretreatment with free hyaluronic acid, and FIG. 7b shows cell viability at different concentrations of HAMBs.

When excess free hyaluronic acid was pre-treated, the NIRF intensity was highly reduced compared to the case without free HA. This result demonstrates that the fast binding of HAMBs to liver cells was based on interaction of HAMBs with CD44 receptors.

In Vivo Biodistribution of HAMBs in Mice

When HAMBs were intravenously injected into mice, their biodistribution was analyzed using optical imaging system. After the injection of HAMBs, the intense NIRF signal was significantly observed in liver site. This signal gradually increased for about 3 hours, showing the high accumulation of HAMBs in liver. On the other hand, the NIRF signal in liver was remarkably reduced when excess free HA was pre-injected for competitive binding to CD44 receptors. This result showed that high accumulation of HAMBs in liver was highly related with the CD44 receptors. 3 hours post-injection of HAMBs, the mice were sacrificed and major organs were analyzed under ex vivo condition.

Figure 8A:
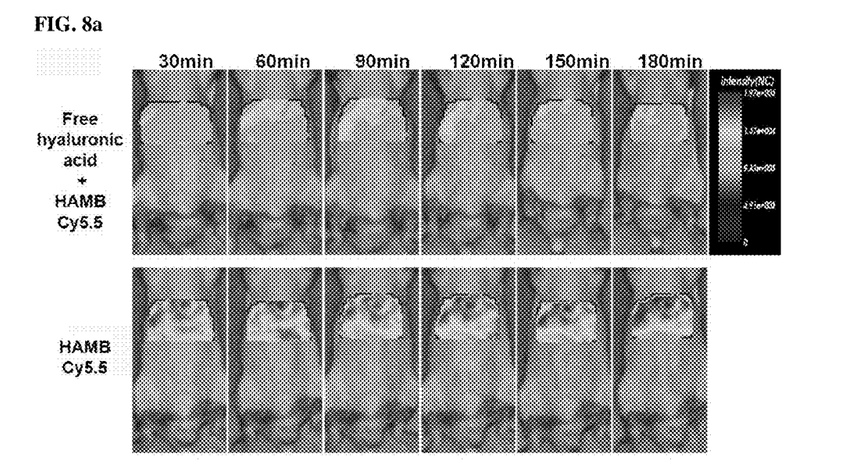
FIG. 8a shows time-dependent fluorescence images of Cy5.5-labeled HAMBs after administration to mice with and without pretreatment with free hyaluronic acid.
Figure 8B:
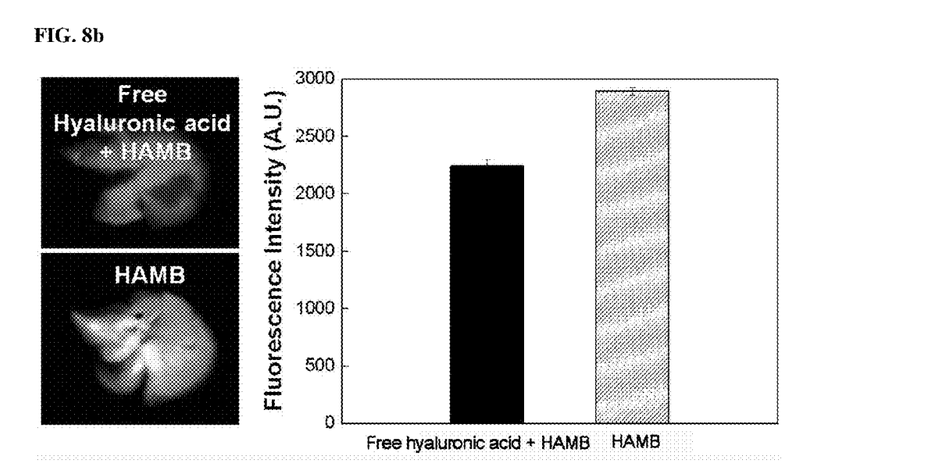
FIG. 8b shows images and a fluorescence intensity graph obtained after the mice were sacrificed 3 hours post-injection of HAMBs and their organs were analyzed under ex vivo condition.

FIG. 8a shows time-dependent fluorescence images of Cy5.5-labeled HAMBs after administration to mice with and without pretreatment with free hyaluronic acid, and FIG. 8b shows images and a fluorescence intensity graph obtained after the mice were sacrificed 3 hours post-injection of HAMBs and their organs were analyzed under ex vivo condition. As expected, the NIRF intensity in liver was highest among all organs, which was higher than any other organs including kidney and spleen.

In vivo ultrasound imaging of liver in normal mice using HAMBs

In vivo ultrasound imaging of liver could be available with HAMBs in mice. After the intravenous injection of HAMBs at 4 mg/ml, liver site was precisely observed and analyzed using Vevo770 ultrasound imaging system.

Figure 9A:
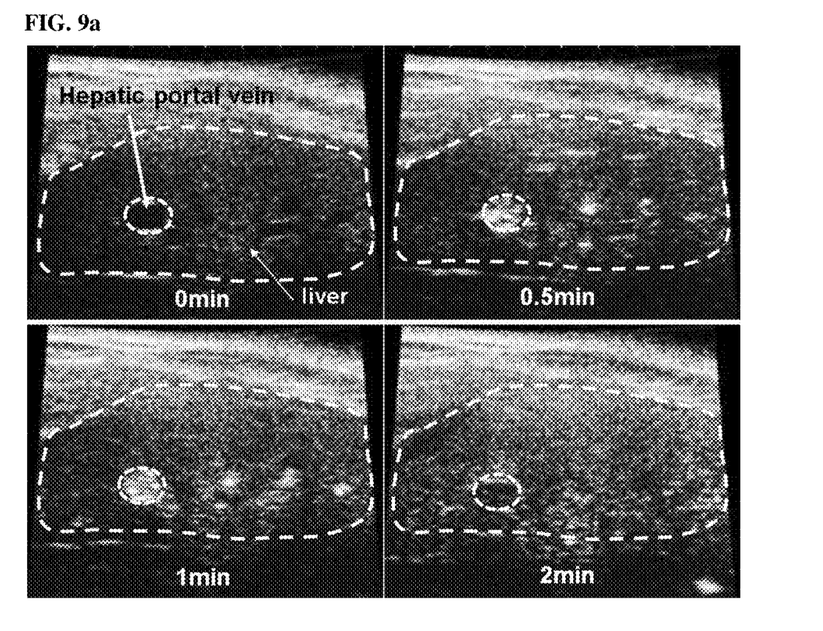
FIG. 9a shows ultrasound images of liver at 0, 0.5, 1, and 2 minutes after administration of HAMBs.
Figure 9B:
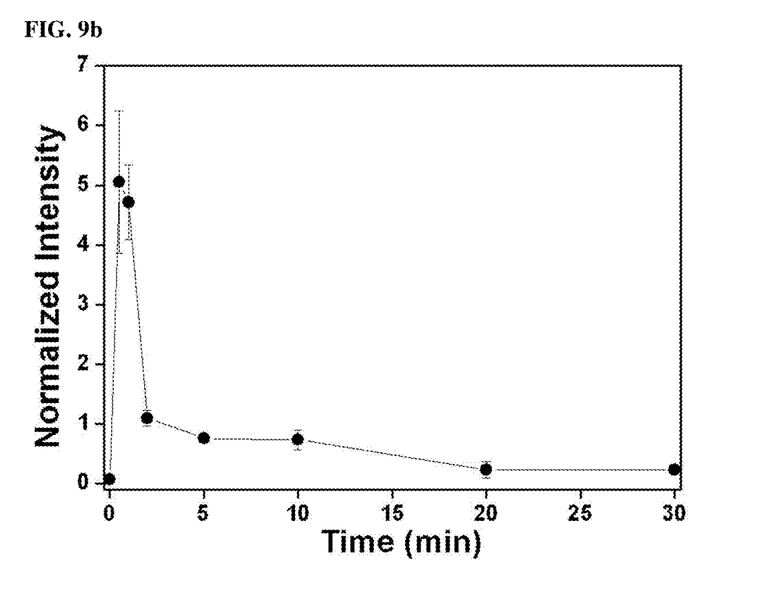
FIG. 9b is a graph showing normalized fluorescence intensity over time.
Figure 10A:
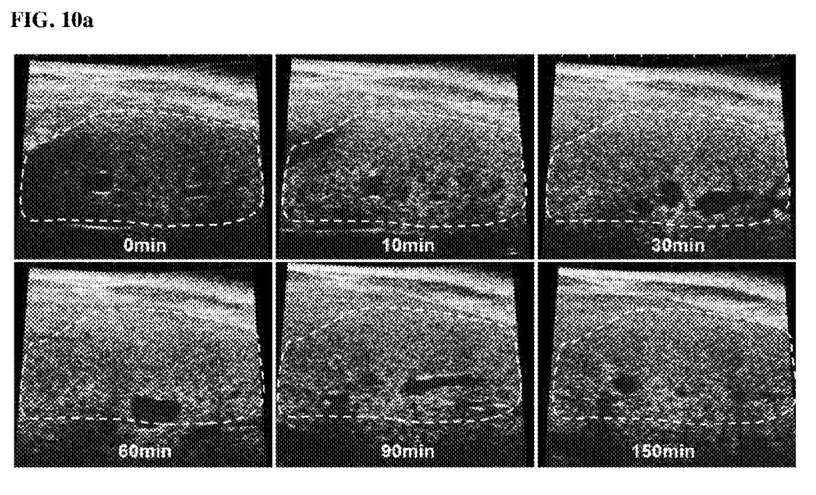
FIG. 10a shows ultrasound images of liver at 0, 10, 30, 60, 90, and 150 minutes after administration of HAMBs.
Figure 10B:
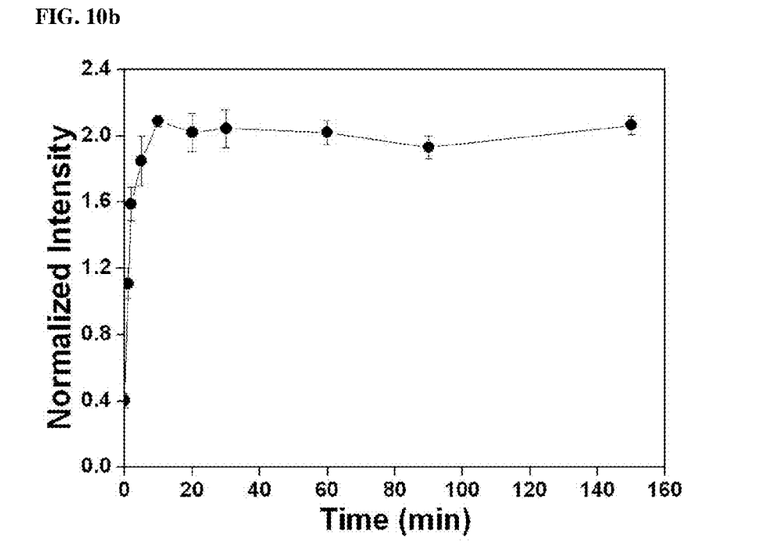
FIG. 10b is a graph showing normalized fluorescence intensity over time.

FIG. 9a shows ultrasound images of liver at 0, 0.5, 1, and 2 minutes after administration of HAMBs, and FIG. 9b is a graph showing normalized fluorescence intensity over time. FIG. 10a shows ultrasound images of liver at 0, 10, 30, 60, 90, and 150 minutes after administration of HAMBs, and FIG. 10b is a graph showing normalized fluorescence intensity over time.

Just after injection of HAMBs, the intense ultrasound signal was observed in portal vein of liver, which was maintained for about one minute. This ultrasound signal intensity in portal vein was about 5.1 fold higher than that before the injection of HAMBs. This result showed the potential of HAMBs as ultrasound contrast agent for blood vessel imaging like other commercial ultrasound agents. The liver site of HAMB-injected mice was further observed, and as a result, the liver tissue gradually became brighter in ultrasound images. Ten minutes post-injection, the ultrasound intensity of liver tissue increased about 4.8 fold higher than that before the injection of HAMBs. At this time, the location of portal veins was significantly observed as negative dark color. It might originate from the penetration and binding of HAMBs in liver tissue and showed that HAMBs can be used for liver tissue imaging by ultrasound. This increased ultrasound signal was maintained for more than 2 hours, showing long-term stability of HAMBs in liver tissue.

In Vivo Ultrasound Imaging of Liver in Liver Tumor-Bearing Mice Using HAMBs

Figure 11A:
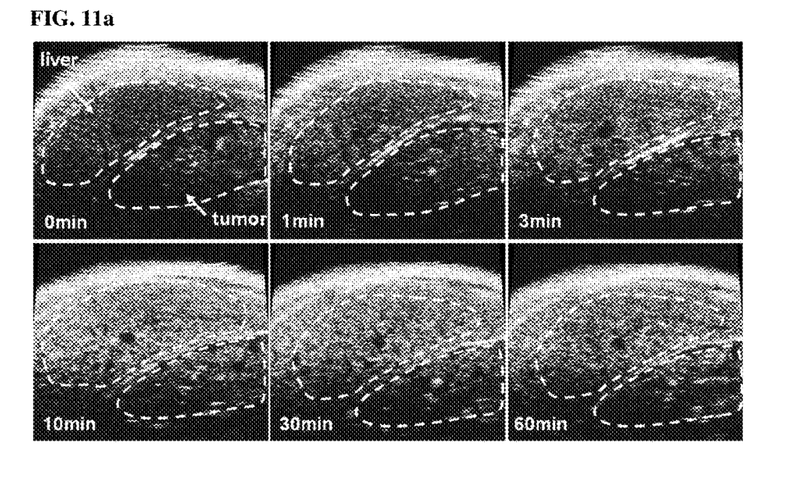
FIG. 11a shows ultrasound images of normal liver tissue and liver tumor tissue observed at 0, 1, 3, 10, 30, and 60 minutes after administration of HAMBs.
Figure 11B:
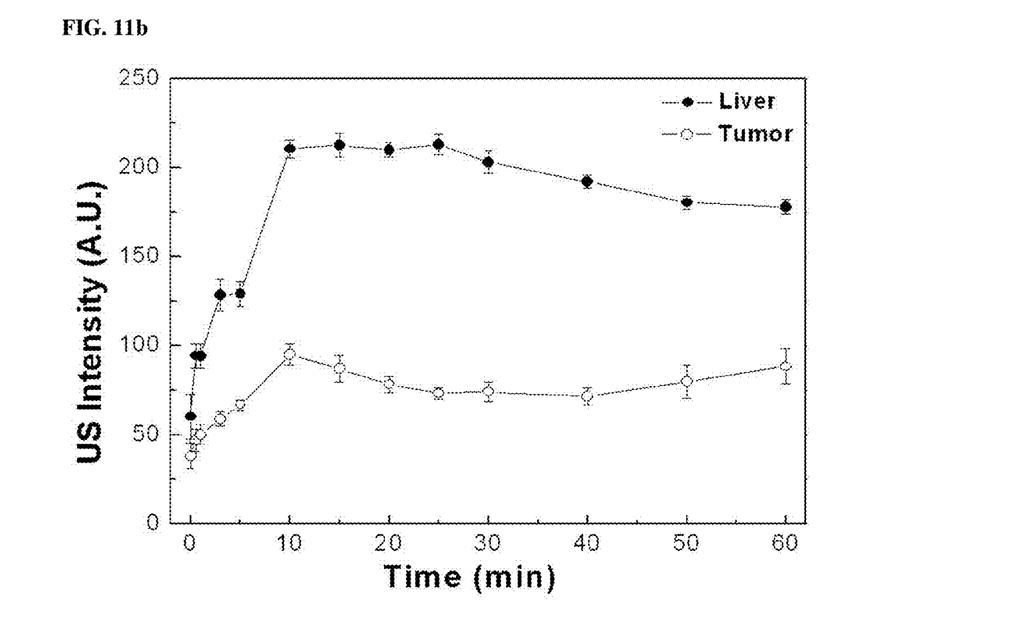
FIG. 11b is a graph showing ultrasound intensity over time.

To test the biomedical potential of HAMBs more precisely, liver tumor-bearing mice models were made by laparotomy and direct injection of HT29 human colonic carcinoma cells into liver. FIG. 11a shows ultrasound images of normal liver tissue and liver tumor tissue observed at 0, 1, 3, 10, 30, and 60 minutes after administration of HAMBs, and FIG. 11b is a graph showing ultrasound intensity over time.

After intravenous injection of HAMBs into these liver tumor models, the ultrasound intensity in liver tissue significantly increased. This increase was more remarkable in normal liver tissue (about 4.0 fold) than tumor tissue (about 2.1 fold). Interestingly, this difference between normal liver tissue and tumor tissue enabled the easy delineation of tumor tissue in liver by ultrasound imaging. This result demonstrates the great potential of HAMBs as ultrasound contrast agent for liver diagnosis.

In summary, hyaluronic acid-coated microbubbles (HAMBs) as ultrasound contrast agent were developed and their biomedical potential under in vitro and in vivo condition was evaluated in the present invention. Amphiphilic HA conjugates could encapsulate perfluoropentane gas in aqueous condition resulting in HAMBs. HAMBs were micrometer-sized and provided sufficient stability for ultrasound signal generation in acoustic field. Especially, the interaction between hyaluronic acid shell and CD44 receptors enabled efficient binding of HAMBs to liver cells. Consequently, HAMBs showed high accumulation in liver site after intravenous injection to mice. During in vivo ultrasound imaging on liver site, HAMBs enabled blood vessel imaging in initial time and liver tissue imaging in late time. These results demonstrate that HAMBs can be successfully used for both blood vessel and liver tissue imaging as ultrasound contrast agent for liver diagnosis.

What is claimed is:

1. A liver tumor-targeting ultrasound contrast agent comprising a gas-generating core and a hyaluronic acid shell, wherein the ultrasound contrast agent comprises 100 parts by volume of the hyaluronic acid shell and 0.08 to 5 parts by volume of the gas-generating core and, wherein the hyaluronic acid is a hydrophobically modified hyaluronic acid.

2. The liver tumor-targeting ultrasound contrast agent according to claim 1, wherein the gas-generating core is a $C_1$-$C_6$ perfluorocarbon compound.

3. The liver tumor-targeting ultrasound contrast agent according to claim 1, wherein the ultrasound contrast agent has an average particle diameter of 400 nm to 4 μm.

4. The liver tumor-targeting ultrasound contrast agent according to claim 1, further comprising a fluorescent marker attached to the hyaluronic acid shell.

5. A method for preparing a liver tumor-targeting ultrasound contrast agent, the method comprising:
hydrophobically modifying hyaluronic acid;
purifying and drying the modified hyaluronic acid, followed by dissolution in deionized water; and
dropping a gas-generating compound into the hyaluronic acid solution,
wherein the gas-generating compound is used in an amount of 0.08 to 5 parts by volume, based on 100 parts by volume of the hyaluronic acid.

6. The method according to claim 5, wherein the hyaluronic acid is hydrophobically modified by reaction with 5β-cholanic acid.

7. The method according to claim 5, wherein the gas-generating compound is a $C_1$-$C_6$ perfluorocarbon compound.

8. The method according to claim 5, further comprising subjecting the mixed solution to sonication after dropping of the gas-generating compound.

* * * * *